United States Patent [19]

Hartwig et al.

[11] Patent Number: 5,239,492
[45] Date of Patent: Aug. 24, 1993

[54] AUTOMATIC INTERNAL CALIBRATION CIRCUIT AND METHOD

[75] Inventors: Robert W. Hartwig, Tacoma; Hodjat Habibi, Duvall, both of Wash.

[73] Assignee: SpaceLabs Medical, Inc., Redmond, Wash.

[21] Appl. No.: 595,613

[22] Filed: Oct. 11, 1990

[51] Int. Cl.$^5$ ...................... G06F 15/46; G01N 31/00
[52] U.S. Cl. ................................ 364/571.01; 364/509; 364/497; 73/1 G
[58] Field of Search .................. 364/571.01, 580, 509, 364/413.03, 497, 498; 73/1 R, 1 G, 4 R, 23.21; 356/437; 250/343

[56] References Cited

U.S. PATENT DOCUMENTS

| | | | |
|---|---|---|---|
| 4,476,706 | 10/1984 | Hadden et al. | 73/1 G |
| 4,494,399 | 1/1985 | Youngman | 73/1 G |
| 4,914,720 | 4/1990 | Knodle et al. | 250/343 |
| 4,947,339 | 8/1990 | Czekajewski et al. | 364/497 |
| 4,953,075 | 8/1990 | Nau et al. | 364/497 |
| 5,013,920 | 5/1991 | Asano et al. | 250/343 |
| 5,060,505 | 10/1991 | Tury et al. | 73/1 G |

Primary Examiner—Thomas G. Black
Assistant Examiner—Michael Zanelli
Attorney, Agent, or Firm—Seed and Berry

[57] ABSTRACT

Apparatus for calibrating the gas detector of a gas analyzer includes a gas source circuit for providing a standard sample gas at a substantially constant, predetermined pressure. The gas source circuit includes a gas bottle for containing the standard sample gas and a pressure regulator circuit for maintaining the output pressure of the gas source circuit to the substantially constant, predetermined pressure. Ideally, the gas source circuit is semipermanently coupled to the gas detector so that calibration may be performed at any time, even while the gas detector is coupled in an analysis circuit for analyzing an unidentified sample gas. The gas analyzer further includes a data processor that responds to programming instructions and data for controlling the gas source circuit and gas detector to perform the zero measurement and span measurement needed for calibration. The data processor is constructed to initiate a calibration operation upon the occurrence of a predetermined event such as, for example, elapse of a predetermined time interval.

40 Claims, 5 Drawing Sheets

AUTOMATIC INTERNAL CALIBRATION CIRCUIT AND METHOD

DESCRIPTION

1. Technical Field

The present invention is directed toward gas detectors and, more particularly, toward method and apparatus for automatic internal calibration of a gas detector.

2. Background of the Invention

Gas detectors are devices which are provided for determining the quantities of specific gases, referred to as target gases, contained in an unidentified sample gas. As an example, gas detectors have been used in medical applications to detect the quantities of carbon dioxide, oxygen, and other gases present in a patient's exhalation and/or inhalation. Gas detectors also find application in laboratory environments where the composition of gases must be determined to further the investigation of the laboratory. Many other applications for gas detectors exist and are known in the art.

The gas detector typically includes data processing circuitry that provides numerical data, referred to as raw data, indicative of the quantities of the target gases in the sample gas. The data processing circuitry is further adapted to convert the raw data and scale it in accordance with predetermined scaling factors to provide numerical values equal to the actual quantities of the target gases in the sample gas.

The scaling factors are determined through a calibration process that includes a zero measurement and a span measurement. The zero measurement is performed by providing a zero sample gas to the gas detector, wherein the zero sample gas includes substantially zero quantities of the target gases to be measured. The raw data generated in response to the zero measurement is indicative of data that will be produced when zero quantities of the target gases are present in the sample gas. The span measurement is performed by providing a calibration sample gas to the gas detector wherein the quantities of the target gases contained in the calibration sample gas are known. The known values of the target gases in the calibration sample gas are referred to as tag values. The raw data generated in response to the span measurement is indicative of data that will be produced when the known quantities of the target gases are present in the sample gas. The gas detector is constructed so that the relationship between the raw data and the quantities of the target gases in the sample gas is linear. Therefore, the zero measurement values and span measurement values can be used in combination with the tag values to determine a scaling factor which will be applicable to all raw data. However, the integrity of the measurement of an unidentified sample gas is dependent upon the accuracy of the scaling factors, and consequently, the accuracy of the calibration.

Prior art methods for calibrating gas detectors rely upon the gas detector being disconnected from the analysis circuit and reconnected to a calibration sample gas source for performing the span measurement. However, removal of the gas detector from the analysis circuit for calibration is not desirable since it requires the user to choose between calibration or continued analysis, i.e., either forego needed calibration or future gas analysis. Accordingly, it is desirable to provide apparatus which is capable of being calibrated without being disconnected from the analysis circuit.

Further, presently available methods for calibrating gas detectors require the user to provide the calibration sample gas to the gas detector at a predetermined pressure. Many users rely upon the dial-type transducer provided with standard gas bottles for determining when the calibration sample gas is being provided at the proper pressure. However, the accuracy of the dial-type transducer and the ability of the user to adjust the dial-type transducer are both far less accurate than the measurement performed by the gas detector. Therefore, the calibration and scaling factors that are generated by the gas detector are only as accurate as the dial-type transducer and crude adjustment provided by the user. Accordingly, it is desirable to provide apparatus for calibrating a gas detector that is capable of accurately controlling the pressure at which the calibration sample gas is provided to the gas detector.

Still further, prior art methods and apparatus for calibrating gas detectors require the user to manipulate a transducer on the gas detector to adjust the raw data to the actual quantities of the target gases contained in the calibration sample gas. This adjustment is required since the gas detector is not otherwise provided with the quantities of the target gases in the calibration sample gas. After the user makes the appropriate adjustment, the gas detector generates the necessary scaling factors for calibration. Again, the accuracy of the scaling factors generated is limited by the user's ability to accurately adjust the raw data to the actual values. Accordingly, it is desirable to provide method and apparatus for calibrating a gas detector wherein it is not necessary for the user to adjust the raw data to actual values of the target gases in the calibration sample gas.

Additionally, the grade of calibration sample gases varies widely with price, i.e., less expensive calibration sample gases typically provide more or less of the target gas than specified. The accuracy of the calibration is therefore also dependent upon the grade, and consequently the price, of the calibration sample gas provided by the user. Accordingly, it is desirable to provide method and apparatus for calibrating a gas detector wherein the cost of accurate calibration can be reduced.

SUMMARY OF THE INVENTION

The present invention is directed toward apparatus and method for calibrating a gas detector of the type wherein the gas detector is responsive to a span signal to perform a span measurement for self-calibration. The invention includes a sample gas source responsive to a control signal for providing a standard sample gas to the gas detector. The standard sample gas contains known quantities of a target gas. The sample gas source is adapted to provide the standard sample gas to the gas detector at a substantially predetermined, constant pressure. The invention further includes a data processor for providing the control signal and the span signal so that the gas detector will determine the quantities of the target gas in the standard sample gas and perform self-calibration.

In alternative embodiments, the data processor is adapted to initiate the self-calibration of the gas detector upon the occurrence of a predetermined event. As an example, the data processor may be adapted to initiate the self-calibration after elapse of a predetermined time interval. In the presently preferred embodiment of the invention, a user interface is provided that includes a start calibration switch as well as a start switch for starting the gas detector. The data processor is responsive to both the start switch and the start calibration switch for initiating the calibration operation.

DETAILED DESCRIPTION OF THE INVENTION

Figure 1:
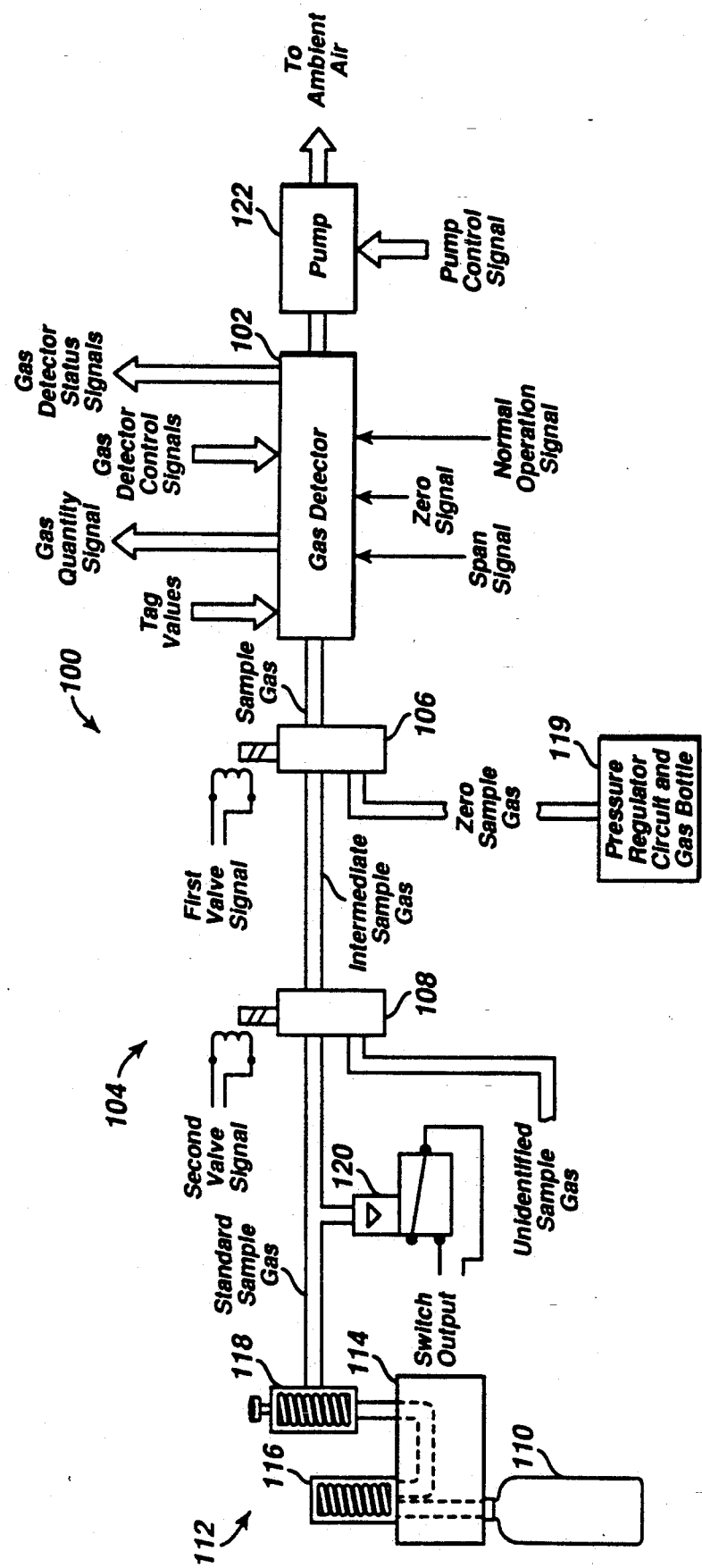
FIG. 1 is a schematic diagram of a pneumatic circuit for a gas analyzer that is the subject of the present invention, including the sample gas source used to calibrate the gas analyzer.
Figure 2:
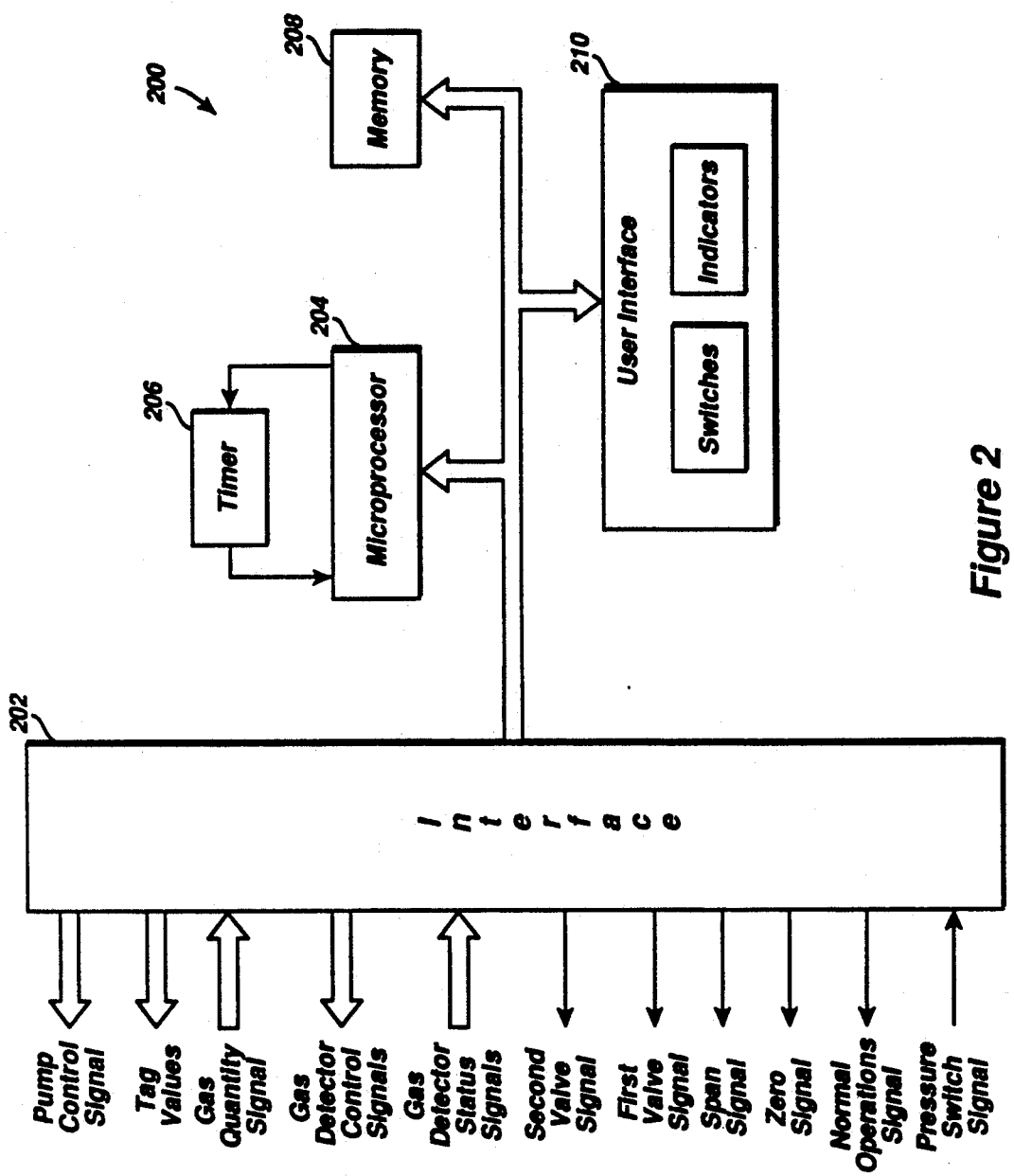
FIG. 2 is an illustrative block diagram of a data processor for controlling the operation of the pneumatic circuit illustrated in FIG. 1.

A gas analyzer includes a pneumatic circuit 100, FIG. 1, and a data processor 200, FIG. 2. The pneumatic circuit 100 includes a gas detector 102 for detecting the quantity of a target gas contained in a sample gas. As is known in the art, the gas detector 102 is constructed for receiving the sample gas and for providing raw data indicative of the quantity of the target gas in the sample gas. The gas detector 102 may also include apparatus for performing span and zero measurements to provide scaling factors for calibration of the gas detector 102, as is also known in the art.

The gas detector 102 is constructed to provide a gas quantity signal to indicate the quantity of the target gas in the sample gas and to receive a tag value from the data processor 200. The gas quantity signal is used by the data processor 200 during calibration and the tag value is used by the gas detector 102 during calibration, as will be discussed in more detail below. The gas detector 102 is also responsive to three control signals, i.e., a normal operation signal, a zero signal and a span signal to perform an analysis of the sample gas. The gas detector 102 is responsive to the normal operation signal to perform its normal function of analyzing an unidentified gas. The gas detector 102 is responsive to the zero signal and the span signal to perform the zero measurement and the span measurement, respectively.

It will be apparent to those skilled in the art, that while the gas detector 102 is described herein as being responsive to three control signals, i.e., the normal operation signal, the zero signal and the span signal, the gas detector 102 could be constructed to operate in the three modes using two signals capable of producing three states. In the presently preferred embodiment of the invention, the gas detector 102 is responsive to the presence of the zero and span signals to perform the zero and span measurements, respectively. The gas detector 102 is further responsive to the absence of the zero and span signals to perform its normal operation. The operation of the gas detector 102 will be described in more detail below.

The gas detector 102 may comprise any apparatus for determining the quantity of a target gas in a sample gas. Further, the gas detector 102 may be adapted to determine the quantity of a single target gas or, alternatively, the gas detector 102 may be constructed for determining the quantities of a plurality of target gases that may be contained in the sample gas. In the presently preferred embodiment of the invention, the gas detector 102 is constructed to determine the quantities of a plurality of target gases in a sample gas. Although the invention is described herein by reference to a gas detector for determining the quantity of a single target gas, those skilled in the art will readily understand and appreciate the application of the invention to a gas detector constructed for determining the quantities of a plurality of target gases in a sample gas.

Further, the gas detector 102 may be of several known types of gas detectors for determining the quantity of a target gas in a sample gas. Gas detectors are generally categorized according to the energy source used. In the presently preferred embodiment of the invention, the gas detector 102 comprises a nondispersive infrared gas detector of the type which uses infrared light as the energy source for determining the quantity of the target gas in the sample gas. Such nondispersive infrared gas detectors may be readily provided by those skilled in the art. It will be apparent, however, to those skilled in the art, that other gas detectors may be substituted for the nondispersive infrared gas detector 102.

Gas detector 102 is coupled to receive the sample gas from a sample gas source circuit 104. The sample gas source circuit 104 is constructed to selectively couple a plurality of gas sources to the gas detector 102 for selectively providing one of a plurality of gases to the gas detector 102 as the sample gas. In the presently preferred embodiment of the invention, the sample gas source circuit 104 is adapted to provide as the sample gas either an unidentified sample gas, a zero sample gas or a standard sample gas. The unidentified sample gas provided by the sample gas source circuit 104 is a gas wherein the quantity of the target gas is unknown. This gas is typically provided during normal operation for analysis by the gas detector 102 to determine the quantities of the target gas contained therein. The zero sample gas is a gas having substantially zero values of the target gas and is used by the gas detector 102 to perform the zero measurement. The standard sample gas is a gas having known quantities of the target gas and is used by the gas detector 102 to perform the span measurement. As will be discussed in more detail below, the standard sample gas is distinguished from the calibration sample gas used in prior art methods of calibration since the standard sample gas remains the same for all calibrations of the gas detector 102.

The sample gas source circuit 104 includes first and second valves 106 and 108, respectively, for selectively coupling the plurality of gas sources to the gas detector 102. First and second valves 106 and 108 each comprise an electromechanical device that is responsive to an electrical signal for selectively coupling an output fluid path to one of two input fluid paths.

First valve 106 is responsive to a first valve signal provided by the data processor 200 illustrated in FIG. 2 for providing as its output either the zero sample gas or an intermediate sample gas provided from the output of the second valve 108. The output from the first valve 106 is coupled directly to the gas detector 102 and provides the sample gas for the gas detector. The first valve signal that controls the operation of the first valve 106 is provided in two states, i.e., a first state wherein the intermediate sample gas is provided to the gas detector 102 as the sample gas, and a second state wherein the zero gas is provided to the gas detector 102 as the sample gas.

In similar fashion, the second valve 108 is responsive to two states of a second valve signal, also provided by the data processor 200, to provide either the unidentified sample gas or the standard sample gas to the first valve 106 as the intermediate sample gas. The second valve signal is also provided in two states, i.e., a first state wherein the second valve 108 couples the unidentified sample gas to the first valve 106 as the intermediate sample gas, and a second state wherein the second valve 108 couples the standard sample gas to the first valve 106 as the intermediate sample gas.

In the presently preferred embodiment of the invention, first and second valves 106 and 108 each comprise solenoid valves wherein an electrical solenoid is responsive to the presence or absence of an electrical signal to multiplex the two input fluid paths to a single output fluid path. It will be apparent, however, to those skilled in the art that many other readily available devices may be substituted for the first and second valves 106 and 108. Further, although the invention is described herein by reference to first and second valves 106 and 108, a single valve may be provided for multiplexing the three input fluid paths to a single output fluid path. In such an embodiment, the single valve would be responsive to an electrical signal capable of providing three different states wherein the single valve is responsive to each state for multiplexing a different input fluid path to its single output fluid path.

Further, in the presently preferred embodiment of the invention pneumatic circuit 100 is constructed for use in a medical facility for determining the composition of a patient's exhalation and/or inhalation. Accordingly, the unidentified sample gas provided to the second valve 108 comprises the exhalation and/or inhalation from a patient under analysis, the patient and apparatus coupling the patient's exhalation and/or inhalation to the second valve 108 comprising the source of the unidentified sample gas. Also, since the pneumatic circuit 100 described herein is adapted to determine the quantity of target gases that are not present in substantial quantities in air, air may be readily used as the zero sample gas. Accordingly, the zero sample gas is provided from the ambient air surrounding the pneumatic circuit 100, the ambient environment and apparatus coupling air from the ambient environment to the first valve 106 comprising the source of the zero sample gas. It will be apparent, however, to those skilled in the art, that the pneumatic circuit 100 could be readily adapted for use in a number of various applications. Further, the gas analyzer could be readily adapted for use to determine the quantities of other target gases. In these other applications, it may be desirable to provide an alternative source for the zero sample gas as will be discussed in more detail below.

As mentioned above, the gas source circuit 104 is constructed to selectively provide gas from a plurality of sources as the sample gas. A particularly novel aspect of the present invention is that the gas source circuit includes a high density gas bottle 110 coupled to a pressure regulator circuit 112, for providing the standard sample gas at a substantially constant, predetermined pressure and flow. The high density gas bottle 110 is provided to contain the standard sample gas. In the presently preferred embodiment of the invention, the high density gas bottle 110 is constructed to be coupled to the remainder of the gas source circuit and mounted within the cabinet of the pneumatic circuit 100 and to remain therein, semipermanently, until empty. In this manner the standard sample gas provided by the gas source circuit 104 remains the same for all calibrations, i.e., the quantity of the target gas contained in the standard sample gas remains unchanged. The standard sample gas provided by the gas source circuit 104 is therefore distinguished from calibration sample gases used in prior art methods since prior art calibration sample gases and the quantity of the target gas in the calibration sample gases change from calibration to calibration.

To enable the high density gas bottle 110 to be used for a multiplicity of calibrations, and thereby reduce the number of times the high density gas bottle 110 need be refilled over the lifetime of the pneumatic circuit 100, the high density gas bottle 110 is constructed to contain the standard sample gas at a very high pressure. In this manner, the volume of the standard sample gas stored in the high density gas bottle 110 is maximized. The high density gas bottle 110 used in the presently preferred embodiment of the invention was specially designed by Scott Medical Products in combination with Amtrol, Inc. to meet predetermined specifications. As designed, the high density gas bottle 110 comprises a cylindrical steel bottle approximately six inches in length and two inches in diameter. The high density gas bottle 110 is constructed to contain about 9.4 L of a predetermined standard sample gas at approximately 900 psi. Although the specifications for the high density gas bottle 110 vary slightly with variation in the standard sample gas that the bottle is constructed to contain, the specifications given above are illustrative of the size and pressure limitations to which the high density gas bottle 110 is constructed.

Since the high density gas bottle 110 is constructed to be coupled to the pneumatic circuit 100 and maintained coupled to the pneumatic circuit 100, the gas detector 102 may be quickly and easily calibrated, even while it is being used in its normal operation, i.e., to identify the quantity of the target gas in the unidentified sample gas from a patient. As will be described in more detail below, the first and second valves 106 and 108 cooperate with the data processor 200 to intermittently couple the standard sample gas provided from the high density gas bottle 110 to the gas detector 102 so that the gas detector 102 may perform the span measurement. Additionally, the first and second valves 106 and 108 cooperate with the data processor 200 to also couple the zero sample gas to the gas detector 102 so that the gas detector 102 can intermittently perform the zero measurement. As is known in the art, the gas detector 102 uses the results from the zero measurement and the span measurement to provide scaling factor for self calibration of the gas detector 102.

Another novel aspect of the gas source circuit 104 is that it is constructed to provide the standard sample gas at a substantially constant, predetermined pressure and flow. As mentioned above, the accuracy of the span measurement is affected by the pressure at which the calibration sample gas is provided to the gas detector. To further improve the accuracy of the span measurement performed by the gas detector 102, and thereby improve the accuracy of the calibration and scaling factors, the pressure regulator circuit 112 of the gas source circuit 104 regulates the pressure of the standard sample gas provided by the high density gas bottle 110.

The pressure regulator circuit 112 includes a high pressure manifold 114 coupled to receive the standard sample gas directly from the high density gas bottle 110. As described above, the standard sample gas contained in the high density gas bottle 110 is maintained at a high pressure of approximately 900 psi. Accordingly, the high pressure manifold 114 is provided as simply a conduction path that is capable of withstanding this high pressure. The pressure regulator circuit 112 further includes a first pressure regulator 116 coupled to the high pressure manifold 114 for receiving the standard sample gas from the high density gas bottle 110. The first pressure regulator 116 is provided for substantially reducing the pressure of the standard sample gas. The output from the first pressure regulator 116 is provided to a second pressure regulator 118 via the high pressure manifold 114. The second pressure regulator 118 is constructed for further reducing the pressure of the standard sample gas provided from the high density gas bottle 110.

In the presently preferred embodiment of the invention, the first pressure regulator 116 is provided for reducing the pressure of the standard sample gas from the high density gas bottle 110 from approximately 900 psi down to approximately 30 psi. The second pressure regulator 118 is provided for further reducing the pressure of the standard sample gas from approximately 30 psi to a substantially constant, predetermined pressure of approximately 1 psi. It will be apparent to those skilled in the art that the predetermined value of the pressure of the standard sample gas provided by the second pressure regulator 118 may vary slightly depending upon the specifications of the gas detector 102. The second pressure regulator 118 should be constructed to provide the standard sample gas at a substantially constant pressure and to within predetermined tolerance values as determined by the gas detector 102.

In the presently preferred embodiment of the invention, the first and second pressure regulators 116 and 118 each comprise piston type pressure regulators that employ a precision spring to accurately control the pressure of the output gas. However, it will be apparent to those skilled in the art, that alternative arrangements may be provided for the pressure regulator circuit 112 without departing from the scope of the present invention. As an example, the second pressure regulator 118 may be converted to a device that provides more precision in the output pressure of the standard sample gas. As an example, a diaphragm-type pressure regulator circuit may be readily employed as the second pressure regulator 118. Alternatively, the first and second pressure regulators may each be coupled directly to the high pressure manifold 114 as is the first pressure regulator 116. Still further, a single pressure regulator may be provided so long as the output pressure remains substantially constant and at the predetermined value.

It will be apparent to those skilled in the art that although the high density gas bottle 110 and the pressure regulator circuit 112 is shown and described herein by reference to a standard sample gas for use in performing the span measurement, an identical high density gas bottle and pressure regulator circuit 119 may be provided for supplying the zero sample gas to the gas detector 102. Such an arrangement may be desirable when the gas detector 102 is constructed to measure target gases that are present in air and, therefore, air cannot be used as the zero sample gas.

The gas source circuit 104 also includes a pressure switch 120 that is coupled to receive the standard sample gas provided by the second pressure regulator 118. The pressure switch 120 is constructed for providing an electrical output when the pressure in the output of the second pressure regulator 118 falls below a predetermined minimal value. In the presently preferred embodiment of the invention, the pressure switch 120 is constructed to determine when the high density gas bottle 110 is empty, i.e., the standard sample gas is substantially depleted therefrom. The switch output provided from the pressure switch 120 is coupled to the data processor 200 of FIG. 2, as will be discussed in more detail below.

The pneumatic circuit 100 includes a pump 122 that is coupled to the gas detector 102 for pumping gas therefrom. The pump 122 is responsive to a pump control signal received from the data processor 200 for operating at various speeds. In the presently preferred embodiment of the invention, the pump 122 is constructed for operating at three various speeds, as will be described in more detail below. The output from the pump 122 is provided as output from the pneumatic circuit 100 and, in the presently preferred embodiment of the invention, is provided to the ambient air. Those skilled in the art will appreciate that the pump 122 may be either a positive pressure pump that precedes the gas detector 102 in the fluid path or a negative pressure pump the follows the gas detector 102 in the fluid path.

With reference to FIG. 2, the data processor 200 that is a portion of the gas analyzer is illustrated. The data processor 200 is constructed to provide the control signals to the pneumatic circuit 100 illustrated in FIG. 1. The data processor 200 further receives status signals from the pneumatic circuit 100 as will be discussed in more detail below. The data processor 200 includes an interface 202 for transmitting control signals to the pneumatic circuit 100 and receiving status signals therefrom. The interface 202 is coupled to a microprocessor 204. The microprocessor 204 controls the operation of the data processor 200 and may comprise any of a variety of standard microprocessor circuits that are constructed to respond to a set of programming instructions and data for performing standard data processing operations. Interface 202 may comprise any of a plurality of devices that are constructed to interface the microprocessor 204 with the pneumatic circuit 100. As an example, interface 202 may comprise analog to digital (A/D) convertors, digital to analog (D/A) convertors, voltage amplifiers, buffers, latches, etc. Interface 200 may readily be provided by those skilled in the art upon selection of the microprocessor 204 and the components of the pneumatic circuit 100.

The microprocessor 204 is coupled to a timer 206 that is provided for timing certain operations of the microprocessor 204, as is known in the art. Additionally, the timer 206 may comprise circuit and apparatus that enable the microprocessor 204 to time the occurrence of outside events, as will be discussed more fully below.

The microprocessor 204 is coupled to a memory circuit 208 for receiving programming instructions and data therefrom. Memory circuit 208 may comprise random access memory (RAM) and/or read only memory (ROM) for recording programming instructions and data, as is known in the art. Further, memory circuit 208 is constructed to temporarily record intermediate data provided by the microprocessor 204 and/or the gas detector 102 (FIG. 1). Accordingly, the memory circuit 208 must include apparatus capable of random access, as is known in the art.

A particularly novel aspect of the present invention is the construction of the memory 208 to record a tag value that indicates the amount of the target gas in the standard sample gas. The tag value is used in combination with the span measurement results to determine the scaling factors for the gas detector 102. The tag value is provided to the memory 208 at the time the high density gas bottle 110, containing the standard sample gas, is coupled to the pneumatic circuit 100 and remains the same for all calibrations until the high density bottle 110 is empty. Accordingly, as will be described below in more detail, the user is not required to make any manual adjustment of the tag value while performing the span measurement. This aspect of the invention furthers the ultimate goal of automating calibration of the pneumatic circuit 100.

The data processor 200 further includes a user interface 210 for interfacing a user with the gas detector 100 and, particularly, the data processor 200. The user interface may include switches for enabling a user to provide signals to the microprocessor 204 and/or indicators for enabling the microprocessor 204 to provide signals to the user. The user interface 210 may comprise other various apparatus for interfacing a user with the microprocessor 204. As examples, the user interface 210 may comprise a cathode ray tube (CRT), a keyboard, a mouse, In the presently preferred embodiment of the invention, the user interface 210 includes an empty indicator that is activated by the microprocessor 204, in response to the pressure switch signal received from the pressure switch 120, to provide an indication to the user that the high density gas bottle 110 is substantially empty. The user interface 210 further includes a start switch and a start calibration switch, as will be discussed in more detail below.

Figure 3A:
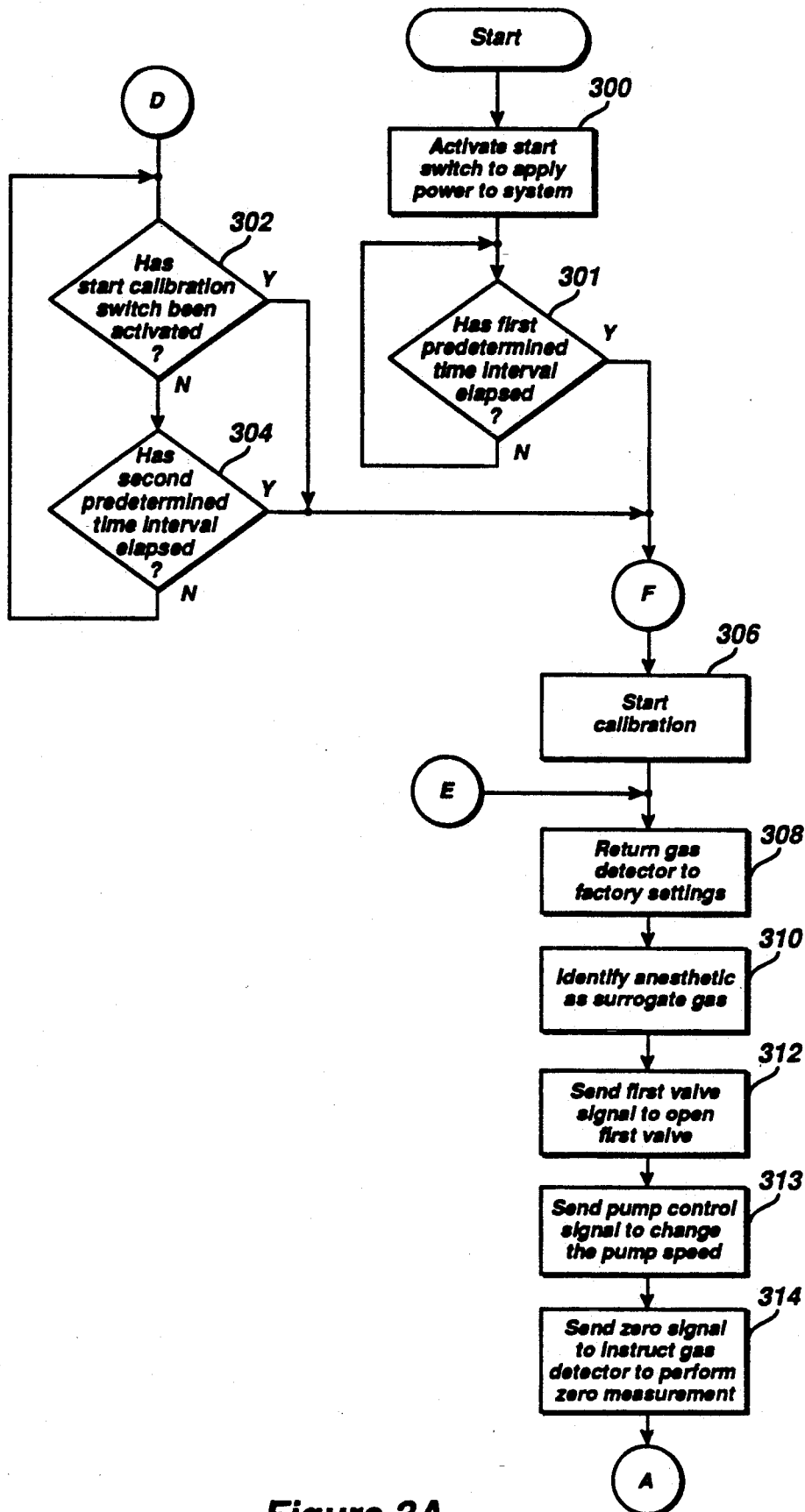
FIGS. 3A, 3B, and 3C are decision flow diagrams illustrating the steps performed by the data processor of FIG. 2.
Figure 3B:
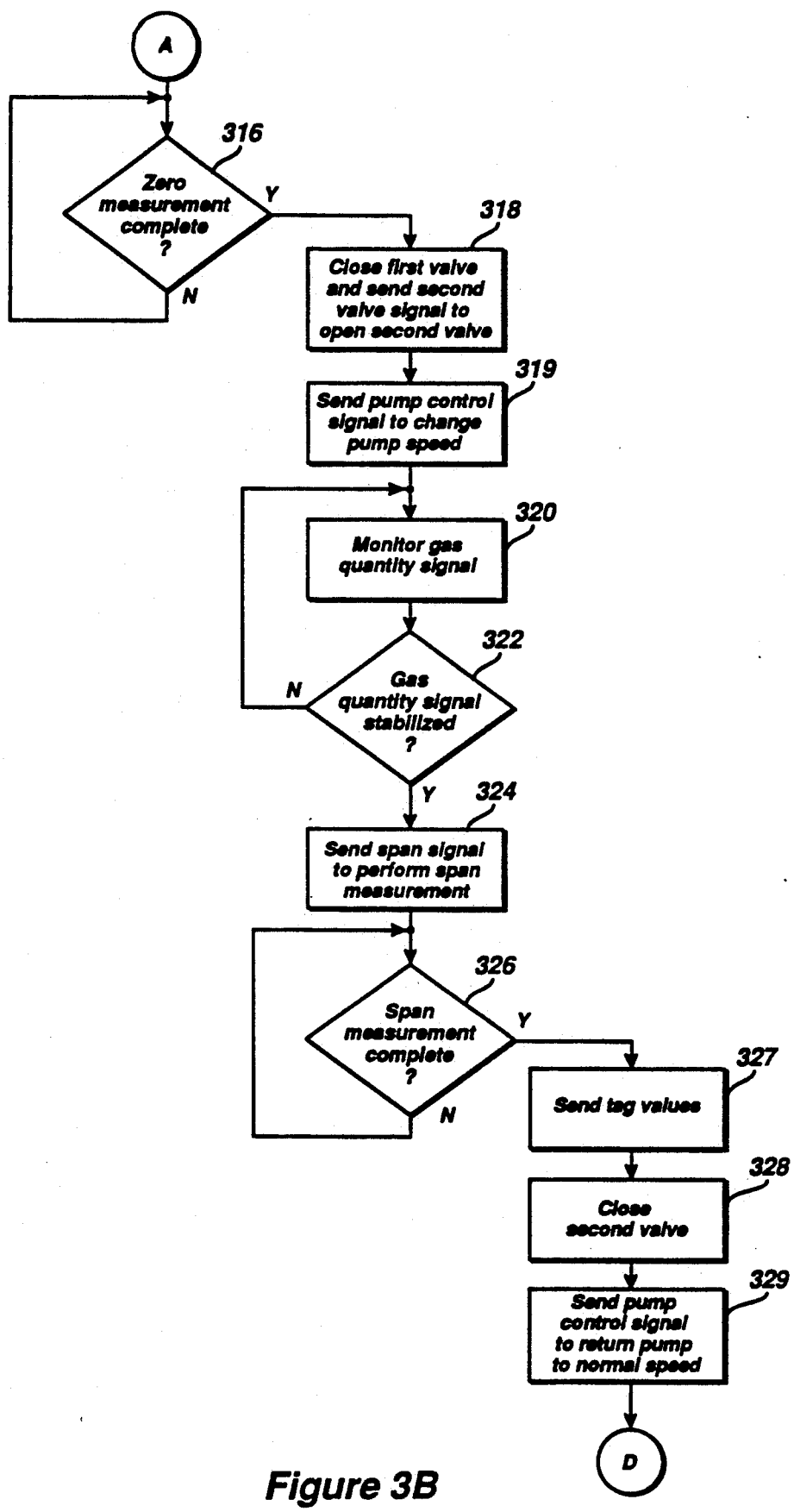
Figure 3C:
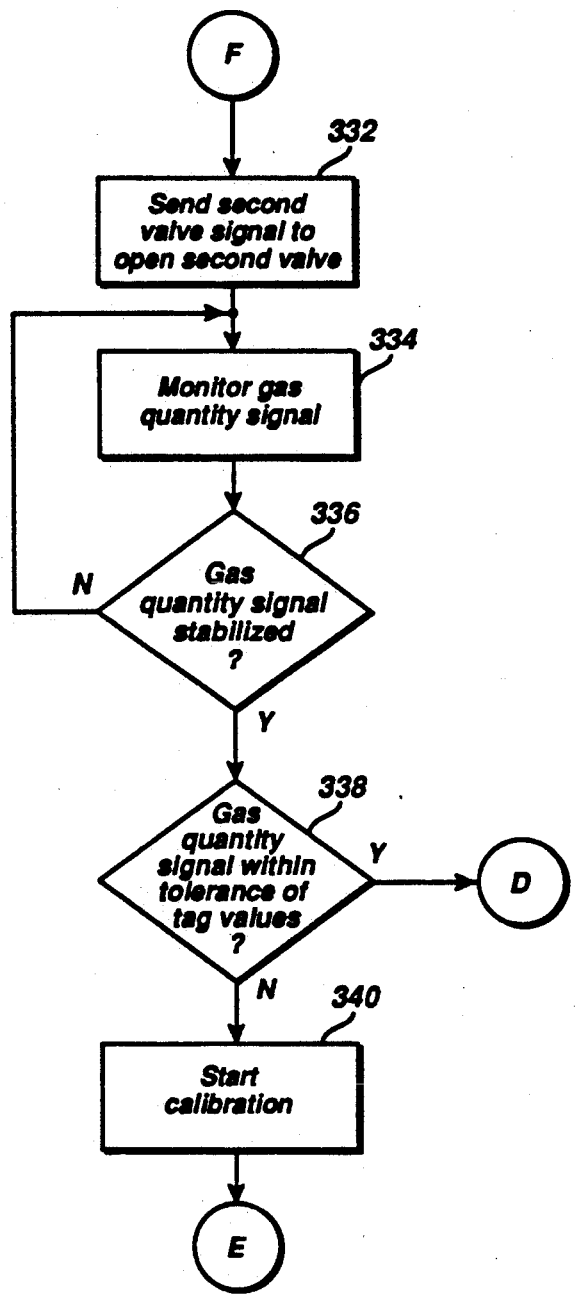

The memory 208 is provided with programming instructions that control the microprocessor 204 to provide signals to the pneumatic circuit 100 of the gas analyzer so that the gas analyzer will be operated in accordance with the illustrative decision flow diagrams of FIGS. 3A, 3B, and 3C. With reference to FIG. 3A, a decision flow diagram is provided that illustrates the manner in which the gas detector 102 (FIG. 1) of the pneumatic circuit 100 is calibrated. Generally, the gas detector 102 is calibrated under control of the data processor 200 upon the occurrence of a predetermined event. In the presently preferred embodiment of the invention three events are used to determine when to calibrate the gas detector 102, i.e., powering the gas analyzer by activating a start switch, a request for calibration by the user by activating a start calibration switch, or the elapse of predetermined time interval selected by the user for automatic calibration.

After power has been applied to the system by activating the start switch, step 300, the data processor 200 begins counting a first predetermined time interval, step 301, prior to beginning the calibration. The start switch is part of the user interface 210 (FIG. 2) and is provided for powering the pneumatic circuit 100 and the data processor 200. The first predetermined time interval is selected to allow the system sufficient time to reach operational equilibrium so that the resulting calibration will be accurate. The timer 206 (FIG. 2) is constructed to measure the first predetermined time interval under control of the microprocessor 202. After the system has had sufficient time to reach operational equilibrium, the data processor 200 will calibrate the gas detector 102, step 306.

As mentioned above, two other events are used to determine when to calibrate the gas detector 102. During operation, i.e., after the system has been powered and calibrated, the data processor 200 continuously determines whether the start calibration switch has been activated, step 302, or a second predetermined time interval has elapsed, step 304. The start calibration switch is also part of the user interface 210 and provided so that the user can request calibration of the gas detector 102 at any time. The second predetermined time interval is a time interval that the manufacturer and/or user of the pneumatic circuit 100 can select as an appropriate interval for calibration of the system. The timer 206 of the data processor 200 is provided for measuring this time interval. As discussed above by reference to the gas source circuit 104, since the standard sample gas is available and capable of being coupled to the gas detector 102 under control of the data processor 200 at any time, the manufacturer and/or user may select any time interval for automatic calibration of the gas detector 102.

It will be apparent to those skilled in the art that although the events described by reference to steps 300, 302, and 304 are the elapse of a predetermined time interval, many other events could be used for calibrating the gas detector at selected times. As an example, the data processor 200 may be constructed to initiate the calibration procedure after a predetermined number of measurements have been made by the gas detector. Other events for initiating the calibration of the gas detector will readily become apparent to those skilled in the art. It will be further apparent to those skilled in the art that although the events for initiating calibration are described herein by reference to the lapse of timers, which create regularly spaced intervals, the events that are used to initiate calibration at selected times may be any event whether or not the time period intermediate calibration are regular intervals.

If any of the events discussed above with respect to steps 300, 302 and 304 have occurred, then the data processor 200 will start the calibration of the gas detector 102, step 306. To begin the calibration operation, the data processor 200 transmits a control signal to the gas detector 102 to return the gas detector 102 to its factory setting, step 308. The factory setting includes predetermined scaling factors that are provided at the factory immediately following manufacture or servicing of the gas analyzer. Returning the gas detector 102 to its factory setting is designed to avoid compounding calibration errors that may have occurred during previous calibration.

In addition to returning the gas detector to its factory setting, the data processor 200 provides a control signal to the gas detector 102 to identify any surrogate gases contained in the standard sample gas, step 310. Since the present invention is provided for medical applications, the gas detector 102 may be constructed to measure as a target gas anesthetic agents in addition to other target gases. It may not, however, be desirable to include the anesthetic agent in the standard sample gas. Accordingly, a surrogate gas may be used in place of the anesthetic agent for calibration purposes. In this case, it is necessary for the data processor 200 to identify the surrogate gas as a target gas for the gas detector 102 prior to calibration. Further, the data processor 200 will receive gas identification data from the gas detector 102 that identifies the actual anesthetic being measured by the gas detector 102. The data processor 102 will record the gas identification data in the memory 208 to be provided to the gas detector 102 at the conclusion of the calibration thereby to return the gas detector to its normal operation.

After any surrogate gases used in the standard sample gas have been identified, the data processor 200 begins the zero measurement by sending the first valve signal to the first valve 106 (FIG. 1), step 312. As discussed above, the first valve signal may be provided in two states, one of which controls the first valve 106 to provide the zero sample gas to the gas detector 102 as the sample gas.

In addition to sending the first valve signal, the data processor 200 also sends the pump control signal to the pump 122, FIG. 1, to change the speed of the pump, step 313. In the presently preferred embodiment of the invention, the speed of the pump 122 is increased thereby to quickly and completely purge the unidentified sample gas from the gas detector 102 to insure that the quantities of the target gas provided to the gas detector 102 by the unidentified sample gas are removed from the gas detector. In this manner, the accuracy of the zero measurement is increased.

After the first valve 106 has been opened and the pump speed increased, the data processor 200 sends the zero signal to the gas detector 102 to instruct the gas detector to perform the zero measurement, step 314. Since the gas detector 102 is receiving the zero sample gas as the sample gas, via the first valve 106, raw data provided by the gas detector 102 in response to the zero measurement will be indicative of the raw value received when a zero quantity of the target gas is present in the sample gas.

With reference to FIG. 3B, the data processor 200 monitors the status signal transmitted to the data processor from the gas detector 102 to determine when the zero measurement has been completed, step 316. When the zero measurement has been completed, the microprocessor 200 will close the first valve 106 so that the sample gas provided to the gas detector 102 will originate from the second valve 108, step 318. The data processor 102 will then send the second valve signal to the second valve 108 so that the second valve 108 will provide the standard sample gas to the gas detector 102 as the sample gas. The data processor 102 will also send the pump control signal to the pump 122 to reduce the speed of the pump 122 to an idle speed, step 319. Reduction of the pump speed to an idle speed allows for conservation of the standard sample gas and also allows the pressure regulator circuit 112 to accurately control the flow of the standard sample gas to the gas detector 102. It will be noted by those skilled in the art that the span measurement of the standard sample gas will not be substantially altered by the presence of the zero gas, as above with respect to the presence of the unidentified sample gas during the zero measurement, since the zero gas contains substantially no quantities of the target gas.

As discussed above, the pressure regulator circuit 112 is constructed to precisely control the pressure at which the standard sample gas is provided to the gas detector 102. Since the composition of the gas contained in the gas detector 102 is changing, the data processor 200 will monitor the gas quantity signal provided by the gas detector 102 to the data processor 200, step 320, to determine whether the gas quantity signal has stabilized, step 322. Awaiting stabilization of the gas quantity signals is necessary, since the values will slowly approach equilibrium after the second valve 108 has been opened. However, since the quantity of the standard sample gas is limited by the size and pressure constraints of the high density gas bottle 110 (FIG. 1), it is desirable to perform the span measurement immediately after the gas quantity signal has stabilized. Accordingly, the data processor 200 is constructred to perform steps 320 and 322 to ensure the integrity of the span measurement while at the same time conserving the quantity of the standard sample gas contained in the high density gas bottle 110.

Once the gas quantity signal has stabilized, the data processor 200 will begin the span measurement by sending the span signal to the gas detector 102, step 324. The data processor 200 will monitor the status signals provided from the gas detector 102 to determine when the span measurement has been completed, step 326. After the span measurement has been completed, the gas detector 102 will begin its calibration.

In order for the gas detector 102 to perform the calibration, the gas detector must be provided with the tag value that has been previously stored in the memory 208 of the data processor 200. The data processor 200 provides the tag value to the gas detector 102, step 327, after performing the span measurement. As is known in the art, zero and span calibrations are performed to associate the raw values produced during the zero and span measurements with zero values and the tag values, respectively. The gas detector 102 will use the results of the zero and span calibrations, in combination with the tag value, to determine the appropriate scaling factors.

After completion of the calibration, the data processor 200 will change the state of the second valve signal to close the second valve 108 so that the sample gas received by the gas detector 102 will be the unidentified sample gas, step 328, and will send the pump control signal to the pump 122 to return the pump 122 to its normal pump speed, step 329. Thereafter, the gas detector 102 returns to its normal operation using the new scaling factors.

In an alternative method for calibrating the pneumatic circuit 100, the data processor 200 may be constructed for performing the subroutine illustrated in FIG. 3C after it has determined that the appropriate event(s) has occurred, as illustrated by steps 300, 302, and 304 of FIG. 3A. In the alternative method, the data processor 200 is constructed to determine whether calibration is necessary, and thereby further conserve the quantity of the standard sample gas contained in the high density gas bottle 110. To this end, the data processor 200 will first send the second valve signal to open the second valve so that the standard sample gas will be received by the gas detector 102 as the sample gas. The data processor 200 will then monitor the gas quantity signal provided by the gas detector 102 to determine when the gas quantity signal has stabilized, steps 334 and 336. After the gas quantity signal from the gas detector 102 has stabilized, the data processor 200 will compare the gas quantity signal to the tag value stored in the memory 208 to determine whether the gas quantity signal is within a predetermined tolerance range of the stored tag value, step 338. If the gas quantity signal is within a predetermined range of the stored tag value, then the microprocessor 200 determines that no calibration is necessary and the algorithm returns to steps 302 and 304 of FIG. 3A. Alternatively, if the gas quantity signal is not within a predetermined tolerance range of the pre-stored tag value, then the microprocessor 200 will start the calibration, step 340, and proceed to step 308 of FIG. 3A.

It will be apparent to those skilled in the art that a particular advantage of the subject invention is that the standard sample gas remains coupled to the gas detector 102 during use thereof, thereby allowing calibration at any time, even times when the pneumatic circuit 100 remains coupled in-circuit with a patient (or other gas analysis circuit). Since the calibration operation is microprocessor controlled and totally automated, user intervention is substantially eliminated, thereby substantially eliminating the number of variables which will affect the integrity of the calibration. Also, data processor control of the calibration allows calibration to be performed in a manner of seconds, thereby allowing quick and easy calibration by the user.

Still further, since the high density gas bottle 110 remains coupled to the gas detector 102, the quantity of the target gas contained in the standard sample gas may be determined with a great deal of precision, yet without undue expense. Such a determination may be made when the original, or a replacement, high density gas bottle 110 is coupled to the pneumatic circuit 100. At that time, a high precision standard sample gas may be provided to the gas detector 102 via the unidentified sample gas input, and used for high precision calibration of the gas detector 102. Thereafter, the tag value of the target gas contained in the standard sample gas stored in the high density gas bottle 110 may be determined to the same degree of accuracy. This tag value can then be stored in the memory 208 of the data processor 200 and thereafter used for later high precision calibration of the gas detector 102. Since the precision of the tag value determined in this manner is related to the precision of the gas detector and the high precision standard sample gas and not the grade of the standard sample gas contained in the high density gas bottle 110, a low grade standard sample gas may be used in the high density gas bottle 110 without impact upon the accuracy of subsequent calibration.

It will be appreciated that, although specific embodiments of the invention have been described herein for purposes of illustration, various modifications may be made without departing from the spirit and the scope of the invention. Accordingly, the invention is not limited except as by the appended claims.

We claim:

1. Apparatus for calibrating a gas detector of the type wherein the gas detector is responsive to a span signal to perform a span measurement for self calibration, said apparatus comprising:
   sample gas source means responsive to a first control signal for providing a standard sample gas to the gas detector, said sample gas source means including bottle means for containing said standard sample gas at a substantially high pressure thereby to permit the size of said bottle means to be minimized and the quantity of said standard sample gas to be maximized relative to the size of said bottle means, said standard sample gas including a target gas of known concentration, said sample gas source means being constructed for providing said standard sample gas to the gas detector at a substantially constant, predetermined pressure;
   data processing means for providing said first control signal to said sample gas source means and for providing the span signal to the gas detector so that the gas detector will determine the quantity of said target gas in said standard sample gas and perform the span measurement for self-calibration.

2. Apparatus as recited in claim 1 wherein said sample gas source means further comprises valve means responsive to said first control signal for coupling said sample gas source means to the gas detector.

3. Apparatus as recited in claim 2 wherein said valve means further comprising means for receiving an unidentified sample gas wherein the quantity of said target gas contained in said unidentified sample gas is unknown, said valve means being responsive to a second control signal to provide said unidentified sample gas to the gas detector, said data processing means for providing said second control signal to enable said gas detector means to determine the quantity of said target gas in said unidentified sample gas.

4. Apparatus as recited in claim 2 wherein the gas detector is also responsive to a zero signal for performing a zero measurement, said valve means further comprising means for receiving a zero sample gas wherein said zero sample gas is a gas having a substantially zero quantity of said target gas, said valve means being responsive to a third control signal for coupling said zero sample gas to the gas detector, said data processing means for providing said third control signal in combination with the zero signal.

5. Apparatus as recited in claim 4 wherein said means for receiving a zero sample gas further comprises means for containing said zero sample gas.

6. Apparatus as recited in claim 4 wherein said means for receiving a zero sample gas further comprises means for receiving ambient air.

7. Apparatus as recited in claim 1 wherein said sample gas source means further comprises pressure regulator means for receiving said standard sample gas at a pressure higher than the substantially constant, predetermined pressure and for reducing the pressure of said standard sample gas to the substantially constant, predetermined pressure.

8. Apparatus as recited in claim 1, further comprising:
   pressure switch means for providing a gas signal wherein said gas signal is indicative of whether said standard sample gas is above a predetermined minimum value; and
   user interface means for interfacing a user with said data processing means, said data processing means being responsive to said gas signal to provide an indication to the user that said bottle means is substantially empty.

9. Apparatus as recited in claim 1 wherein said data processing means further comprises memory means for storing a tag value that identifies the quantity of said target gas in said standard sample gas, said data processing means for providing said tag value to the gas detector.

10. Apparatus as recited in claim 9 wherein the gas detector is also responsive to a normal operation signal to provide a gas quantity signal indicative of the quantity of said target gas present in a sample gas, said data processing means further comprising means for comparing the gas quantity signal to said tag value and for providing the span signal and said first control signal if the gas quantity signal is not within a predetermined range of said tag value.

11. Apparatus as recited in claim 9 wherein the gas detector is also responsive to a normal operation signal to provide a gas quantity signal indicative of the quantity of said target gas present in a sample gas, said data processing means further comprising means for monitoring the gas quantity signal, said data processing means for providing said first control signal and to provide the span signal when the value of the gas quantity signal has stabilized.

12. Apparatus as recited in claim 1 wherein said data processing means further comprises memory means for storing programming instructions, said data processing means being responsive to said programming instructions to periodically provide said first control signal and the span signal.

13. Apparatus as recited in claim 1 wherein said data processing means further comprises memory means for storing programming instructions, said data processing means being responsive to said programming instructions to provide said first control signal and the span signal at predetermined intervals.

14. Apparatus as recited in claim 1 wherein said data processing means further comprises user interface means for interfacing a user with said data processing means, said user interface means including a start calibration switch operable by the user, said data processing means being responsive to said start calibration switch for providing said first control signal and the span signal.

15. Apparatus as recited in claim 1 wherein said data processing means further comprises user interface means for interfacing a user with said data processing means, said user interface means including a start switch operable by the user to start the gas detector, said data processing means being responsive to said start switch for providing said first control signal and the span signal.

16. Apparatus for analyzing a fluid composition to measure the quantity of a specified gas in the fluid composition, said apparatus comprising:
  gas detector means for determining the quantity of a target gas in a sample gas and for providing a quantity output signal indicative of the quantity of said target gas present in said sample gas;
  input means for receiving an unidentified sample gas to be analyzed wherein the quantity of said target gas present in said unidentified sample gas is not known;
  a first valve having a sample gas output, a first valve control input, a first valve normal input and a first valve energized input, said first valve control input for receiving a first valve signal wherein said first valve signal is an electrical signal for controlling the operation of said first valve, said first valve output being coupled to said gas detector means for providing said sample gas thereto, said first valve energized input being coupled to receive ambient air, said first valve being responsive to a first state of said first valve signal to conduct said ambient air to said first valve output so that said ambient air is received by said gas detector means as said sample gas;
  a second valve having a second valve output, a second valve control input, a second valve normal input and a second valve energized input, said second valve control input for receiving a second valve signal wherein said second valve signal is an electrical signal for controlling the operation of said second valve, said input means including coupling means for conducting said unidentified sample gas to said second valve normal input of said second valve, said second valve being responsive to a first state of said second valve signal to conduct said unidentified sample gas from said second valve normal input to said second valve output so that said unidentified sample gas is provided as an intermediate sample gas, said first valve normal input being coupled to said second valve output for receiving said intermediate sample gas, said first valve being responsive to a second state of said first valve signal to conduct said intermediate sample gas from said first valve normal input to said first valve output so that said intermediate sample gas is provided to said gas detector means as said sample gas;
  a high density gas bottle constructed to contain a substantially high quantity of gas at a substantially high pressure thereby to permit the size of the bottle to be minimized, said high density gas bottle being provided for containing a standard sample gas having a predetermined quantity of said target gas;
  high pressure regulator means for substantially reducing the pressure of said standard sample gas, said high pressure regulator means including a high pressure manifold, said high pressure manifold being coupled to said high density gas bottle for receiving said standard sample gas and for conducting said standard sample gas to said high pressure regulator means, said high pressure regulator means providing as its output said standard sample gas at a substantially constant, predetermined pressure;
  conducting means for conducting said standard sample gas from the output of said high pressure regulator means to said second valve energized input of said second valve, said second valve being responsive to a second state of said second valve signal to conduct said standard sample gas from said second valve energized input to said second valve output so that said standard sample gas is provided as said intermediate sample gas;
  a pump having a pump input coupled to said gas detector means and a pump output coupled external to the gas analyzing apparatus, said pump having first and second speeds and being responsive to a pump speed signal to operate in said second speed;
  memory means for storing programming instructions and data, said data including a tag value that identifies the respective quantity of said target gas in said standard sample gas; and
  data processing means responsive to said programming instructions for periodically providing a zero signal, a span signal, and said first and second valve signals to initiate a zero and span measurement for calibration of said gas detector means, said data processing means for providing said first valve signal in said first state and to provide said zero signal to initiate said zero measurement, said gas detector means being responsive to said zero signal to determine the quantity of said target gas present in said ambient air provided to said gas detector means by said first valve and to record the determined quantity as a zero measurement value, said data processing means for providing said first valve signal in said second state and to provide said second valve signal in said second state to initiate said span measurement, said data processing means further for providing said pump speed signal in combination with said second state of said second valve to operate said pump in said second speed, said data processing means for monitoring said quantity output signal provided by said gas detector means to determine when the measurement of the quantity of said target gas in said standard gas sample stabilizes and, thereafter, to provide said span signal to said gas detector means, said gas detector means being responsive to said span signal to determine the quantity of said target gas in said standard sample gas and to record the determined quantities as spam measurement values, said data processing means for providing said tag value to said gas detector means whereby said gas detector means uses said tag value in combination with said span measurement values and said zero measurement values as indices for its calibration.

17. Apparatus as recited in claim 16 wherein said gas detector is constructed to measure the quantity of a second target gas in said sample gas and wherein said standard sample gas further includes a surrogate second gas, said memory means being further constructed to record surrogate identification data to indicate the identify of said surrogate second gas, said data processing means further for providing said surrogate identification data in combination with said second state of said valve to identify said surrogate second gas and to record second gas identification data received from said gas detector means that identifies said second gas, said gas detector means for providing a span response signal to indicate the completion of said span measurement, said data processing means being responsive to said span response signal to provide said second gas identification data to said gas detector means.

18. Apparatus as recited in claim 16, further comprising:
a pressure switch including a pressure input coupled to said coupling means for sampling the pressure of said standard sample gas, said pressure switch also including a switch output for providing a gas signal wherein said gas signal is an electrical output signal that indicates whether the pressure of said sample gas is above a predetermined minimum value; and
user interface means for interfacing a user with said analyzing apparatus, said data processing means being responsive to said gas signal to provide an indication to the user that said high density gas bottle is substantially empty.

19. Apparatus as recited in claim 16, further comprising user interface means for interfacing a user with said analyzing apparatus, said user interface means including a start calibration switch operable by the user to provide a start calibration signal to said data processing means, said data processing means being responsive to said start calibration signal for controlling the operation of said gas detector means and said first and second valves to initiate said zero and span measurements thereby to calibrate said gas detector means.

20. Apparatus as recited in claim 16, further comprising user interface means for interfacing a user with said analyzing apparatus, said user interface means including a start switch operable by the user to provide a start signal for starting the operation of said analyzing apparatus, said data processing means being responsive to said start signal for controlling the operation of said gas detector means and said first and second valves to initiate said zero and span measurements thereby to calibrate said gas detector means.

21. Apparatus as recited in claim 20 wherein said data processing means further includes timing means for measuring a predetermined time interval, said data processing means for controlling the operation of said gas detector means and said first and second valves to initiate said zero and span measurements thereby to calibrate said gas detector means after elapse of said predetermined time interval.

22. Apparatus as recited in claim 16 wherein said high pressure regulator means further comprises first and second pressure regulators, said pressure regulator being coupled to said high pressure manifold to receive said standard sample gas from said high density gas bottle, said second pressure regulator being coupled to receive the output from said first pressure regulator, said regulator means output being provided by said second pressure regulator.

23. Apparatus as recited in claim 16 wherein said high density gas bottle is constructed to contain a gas at a pressure of at least 300 pounds per square inch.

24. Apparatus as recited in claim 16 wherein said high pressure regulator means is constructed for providing a regulated pressure output of no more than 5 pounds per square inch from a pressure input of at least 300 pounds per square inch.

25. Apparatus for analyzing a fluid composition to measure the quantity of specified gases in the fluid composition, said apparatus comprising:
gas detector means for determining the quantity of a target gas in a sample gas, said gas detector means being responsive to a zero signal to perform a zero measurement and being responsive to a span signal to perform a span measurement and subsequent calibration;
a high density gas bottle constructed to contain a substantially high quantity of gas at a substantially high pressure thereby to permit the size of said high density gas bottle to be minimized, said high density gas bottle for containing a standard sample gas having a predetermined quantity of said target gas;
high pressure regulator means coupled to said high density gas bottle for receiving said standard sample gas and for substantially reducing the pressure of said standard sample gas, said regulator means including a regulator output and being constructed for providing said standard sample gas to said regulator output at a predetermined pressure;
valve means coupled to said regulator means and responsive to a first control signal for providing said standard sample gas to said gas detector means, said valve means including means for receiving an unidentified sample gas wherein the quantity of said target gas contained in said unidentified sample gas is unknown, said valve means being responsive to a second control signal for providing said unidentified sample gas to said gas detector means, said valve means further including means for receiving a zero sample gas wherein said zero sample gas contains a substantially zero quantity of said target gas, said valve means being responsive to a third control signal for providing said zero sample gas to said gas detector means;
memory means for storing programming instructions and data, said data including a tag value that identifies the quantity of said target gas in said standard sample gas; and
data processing means responsive to said programming instructions stored in said memory means for periodically providing said zero signal, said span signal, and said first, second and third control signals to control the operation of said gas detector means and said valve means to initiate said zero and span measurements thereby to calibrate said gas detector means, said data processing means for providing said second control signal to enable analysis of the quantity of said target gas in said unidentified sample gas, said data processing means for providing said zero signal and said third control signal to initiate said zero measurement, said gas detector means being responsive to said zero signal to determine the quantity of said target gas present in said zero sample gas provided to said gas detector means by said valve means and to record the determined values as zero measurement values, said data processing means for providing said span signal and said first control signal to initiate said span measurement, said gas detector means being responsive to said span signal to determine the quantity of said target gas in said standard sample gas provided by said valve means and to record the determined quantities as span measurement values, said memory means being responsive to said gas detector means to provide said tag value to said gas detector means whereby said gas detector means uses said tag value in combination with said span measurement values and said zero measurement values as indices for its calibration.

26. Apparatus as recited in claim 25, further comprising:
pressure switch means coupled intermediate said high pressure regulator means and said valve means for sampling the pressure of said standard sample gas and for providing a gas signal wherein said gas signal is indicative of whether said standard sample gas is above a predetermined minimum value; and
user interface means for interfacing a user with said analyzing apparatus, said data processing means being responsive to said gas signal to provide an indication to the user that said high density gas bottle is substantially empty.

27. Apparatus as recited in claim 25, further comprising user interface means for interfacing a user with said analyzing apparatus, said user interface means including a start calibration switch operable by the user to provide a start calibration signal to said data processing means, said data processing means being responsive to said start calibration signal for controlling the operation of said gas detector means and said valve means to initiate said zero and span measurements thereby to calibrate said gas detector means.

28. Apparatus as recited in claim 25, further comprising user interface means for interfacing a user with said analyzing apparatus, said user interface means including a start switch operable by the user to provide a start signal for starting the operation of said analyzing apparatus, said data processing means being responsive to said start signal for controlling the operation of said gas detector means and said valve means to initiate said zero and span measurement thereby to calibrate said gas detector means.

29. Apparatus as recited in claim 25 wherein said data processing means further includes timing means for measuring a predetermined time interval, said data processing means being further constructed for initiating said zero and span measurement after elapse of said predetermined time interval.

30. Apparatus as recited in claim 25, further comprising pump means for pumping said sample gas from said analyzer apparatus, said pump means being responsive to first and second pump control signals to operate at first and second pump speeds, respectively, said data processing means being constructed for providing said first and second pump speed signals in combination with said zero and span signals, respectively.

31. Apparatus as recited in claim 25 wherein said gas detector means further comprises means for providing a gas quantity signal indicative of the quantity of said target gas present in said sample gas, said data processing means for monitoring said gas quanity signal and to provide said span signal to initiate said span measurement after said gas quantity signal has reached a stable value.

32. Apparatus as recited in claim 31 wherein said data processing means further comprises comparison means for comparing said gas quantity signal to said tag value, said data processing means for providing said span signal only if said gas quantity signal is not within a predetermined range of said tag value.

33. Apparatus as recited in claim 25 wherein said gas detector means further comprises means for providing a gas quantity signal indicative of the quantity of said target gas present in said sample gas, said data processing means including means for comparing said gas quanity signal to said tag value to determine whether said gas detector means should be calibrated, said data processing means for initiating said span measurement if said gas quantity signal is not within a predetermined range of said tag value.

34. Apparatus as recited in claim 25 wherein said means for receiving said zero sample gas comprises container means for containing said zero sample gas.

35. Apparatus as recited in claim 25 wherein said means for receiving said zero sample gas comprises means for receiving ambient air.

36. A method for operating a gas analyzer for calibrating a gas detector of the type that responds to a span signal to perform a span measurement, the method being further for operating the gas analyzer so that the gas analyzer performs a self calibration operation, said gas analyzer being further constructed for providing a gas quantity signal indicative of the quantity of the target gas in a sample gas, said method comprising the steps of:
(a) recording a tag value indicative of the quantity of a target gas contained in a standard sample gas, the tag value being recorded so that it is accessible by the gas analyzer;
(b) the gas analyzer coupling the gas detector to a standard sample gas source at selected times for providing the standard sample gas to the gas detector;
(c) the gas analyzer controlling the pressure at which the standard sample gas is provided to the gas detector to within predetermined tolerances;
(d) monitoring the gas quantity signal while performing steps (a)-(c) to determine whether its value is within predetermined tolerances of the tag value and if not, performing step (e); and
(e) the gas analyzer providing the span signal and the tag value to the gas detector so that the gas detector will perform the span measurement.

37. The method as recited in claim 36 wherein the gas detector is further adapted to provide a gas quantity signal indicative of the quantity of the target gas in a sample gas, said method further comprising the steps of:

(f) monitoring the value of the gas quantity signal and performing step (g) when the value of the gas quantity signal has stabilized; and (g) determining whether the value of the gas quantity signal is within predetermined tolerances of the tag value and, if not, performing step (e).

38. The method as recited in claim 37, further comprising the step of:

(h) automatically performing steps (f)-(g) in response to activation of a switch by a user.

39. The method as recited in claim 36 wherein the gas detector is further adapted to provide a gas quantity signal indicative of the quantity of the target gas in a sample gas, said method further comprising the step of:

(f) monitoring the values of the gas quantity signal and performing step (e) when the values of the gas quantity signal have stabilized.

40. The method as recited in claim 36, further comprising the step of:

(f) automatically performing steps (a)-(e) in response to activation of a switch by a user.

* * * * *